United States Patent
Suni et al.

[11] Patent Number: 5,590,166
[45] Date of Patent: Dec. 31, 1996

[54] MAMMOGRAPHY UNIT

[75] Inventors: Jarmo Suni, Espoo; Petri Rantanen, Tuusula, both of Finland

[73] Assignee: Instrumentarium Corporation, Finland

[21] Appl. No.: 579,220

[22] Filed: Dec. 28, 1995

[51] Int. Cl.[6] ........................................ A61B 6/04
[52] U.S. Cl. ............... 378/37; 378/196; 378/197
[58] Field of Search ............... 378/37, 195–197

[56] References Cited

U.S. PATENT DOCUMENTS

| | | | |
|---|---|---|---|
| 5,099,503 | 3/1992 | Strommer | 378/37 |
| 5,335,257 | 8/1994 | Stunberg | 378/37 |

FOREIGN PATENT DOCUMENTS

| | | |
|---|---|---|
| 387475 | 9/1990 | European Pat. Off. |
| 435837 | 7/1991 | European Pat. Off. |
| 564843 | 10/1993 | European Pat. Off. |
| 80586 | 7/1990 | Finland |

*Primary Examiner*—Craig E. Church
*Attorney, Agent, or Firm*—Andrus, Sceales, Starke & Sawall

[57] ABSTRACT

The invention relates to a mammography unit, comprising a C-arm which is mounted on a turning axle (2) adapted to be vertically (arrow C) movable on an upright column (1) and which is pivotable about the turning axle (2) (arrow D), one leg (3) of said C-arm being provided with an X-ray tube (4) and the opposite leg (5) with an image receptor, and said unit further comprising a compression element (6) for compressing the breast to be imaged against the image receptor. The C-arm is further adapted to move linearly (arrow A) in substantially radial directions in the direction transverse to the turning axle (2). The unit comprises elements (20, 21) for controlling the linear motorized movement of the C-arm (arrow A) and the relative compressive movement of the compression element (6) (arrow B) to occur simultaneously at a substantially equal speed for compressing the breast between the compression element and the image receptor.

6 Claims, 5 Drawing Sheets

MAMMOGRAPHY UNIT

BACKGROUND OF THE INVENTION

The present invention relates to a mammography unit, comprising a C-arm which is mounted on a turning axle adapted to be vertically movable on an upright column and which is pivotable about the turning axle, one leg of said C-arm being provided with an X-ray tube and the opposite leg with an image receptor, and said unit further comprising a compression element for compressing the breast to be imaged against the image receptor, said C-arm being further adapted to move linearly in substantially radial directions in the direction transverse to the turning axle.

One drawback in the available mammography units is that compression of the breast with a compression element inflicts pain on a patient and, in addition, some of the breast area remains outside the imaging range. This drawback can be alleviated by moving the C-arm of a mammography unit linearly along the upright column together with the turning axle. However, this is only possible in vertical imagings.

SUMMARY OF THE INVENTION

An object of the present invention is to provide a mammography unit, wherein displacement of the C-arm is possible also in diagonal imagings. Another object of the invention is to provide an arrangement, wherein the C-arm and the compression element can be shifted simultaneously towards each other at a substantially equal traveling speed regardless of the movement factors of the compression element (compression resistance) for developing a uniform compression above and below the breast. In order to achieve these objects, according to one aspect of the invention there is provided a mammography unit, comprising a C-arm which is mounted on a turning axle adapted to be vertically (arrow C) movable on an upright column and which is pivotable about the turning axle (arrow D), one leg of said C-arm being provided with an X-ray tube and the opposite leg with an image receptor, and said unit further comprising a compression element for compressing the breast to be imaged against the image receptor, said C-arm being further adapted to move linearly (arrow A) in substantially radial directions in the direction transverse to the turning axle, in which unit the compression element is mounted on the C-arm and travels essentially linearly relative to the C-arm lengthwise of the C-arm and simultaneously with the C-arm radially relative to the turning axle, said unit comprising elements for controlling the linear motorized movement of the C-arm (arrow A) and the relative compressive movement of the compression element (arrow B) to occur simultaneously at a substantially equal but oppositely directed speed for compressing the breast between the compression element and the image receptor.

BRIEF DESCRIPTION OF THE DRAWINGS

The invention will now be described with reference made to the accompanying drawings, in which.

DETAILED DESCRIPTION OF THE PREFERRED EMBODIMENT

Figure 1:
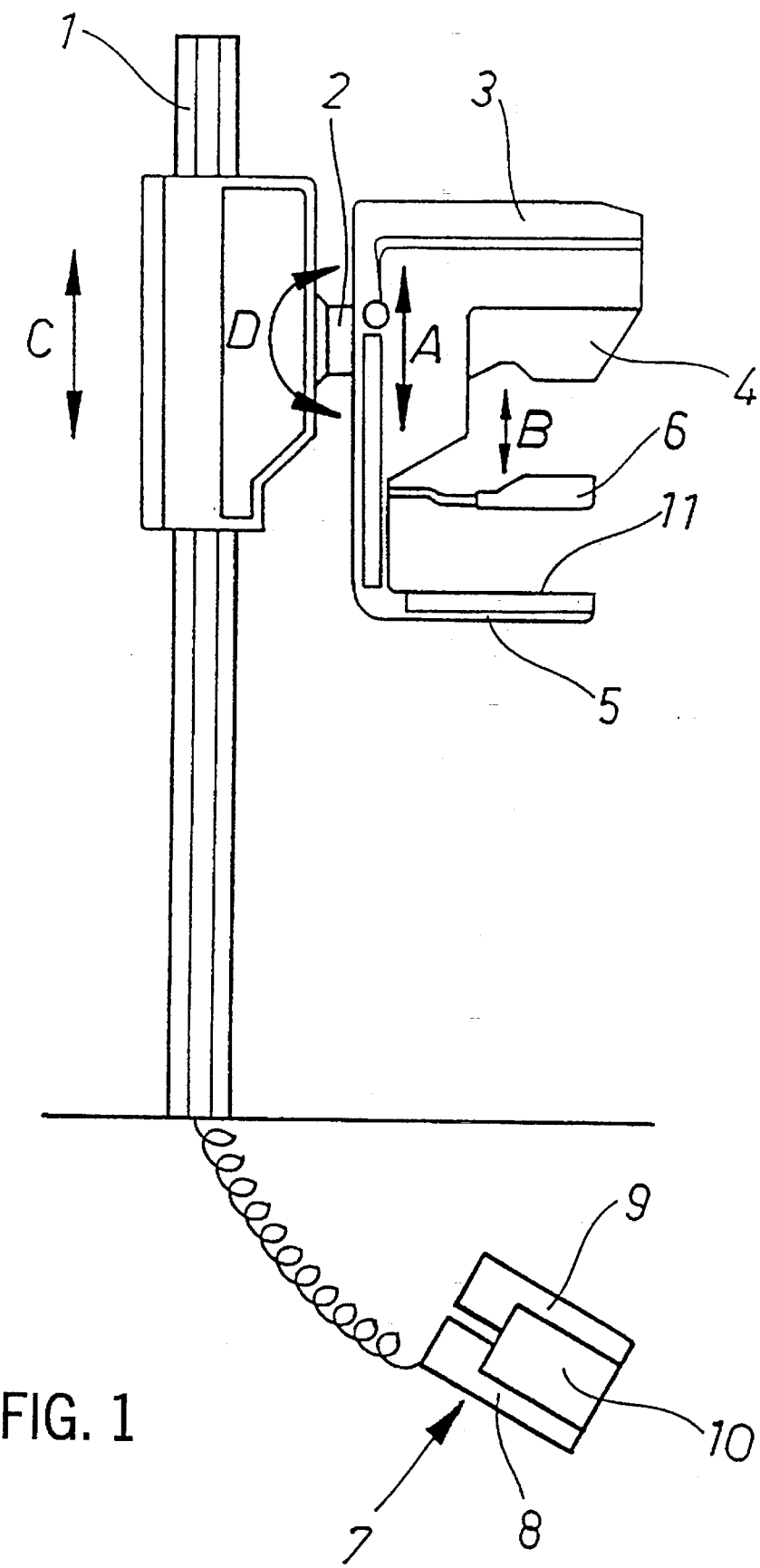
FIG. 1 is a schematic side view of a mammography unit of the invention.
Figure 4:
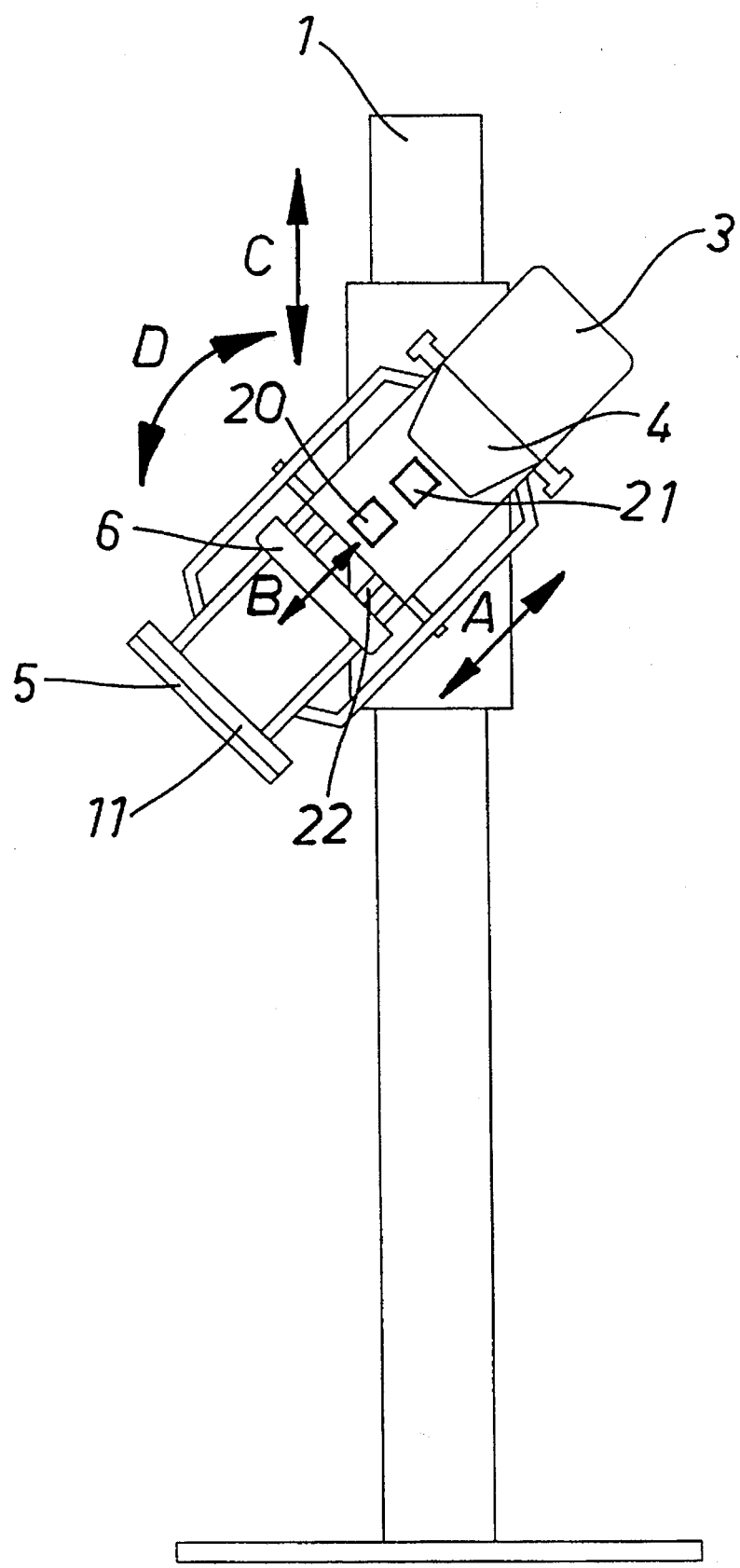
FIG. 4 shows schematically the unit of FIG. 1 in a front view with the C-arm in a diagonal imaging position.

According to FIGS. 1 and 4, the unit includes an upright column 1, fitted with a vertically (arrow C) mobile turning axle 2, in turn fitted with a C-arm which is pivotable about the turning axle (arrow D). The C-arm has an upper leg 3 provided with an X-ray tube head 4 and an opposite leg 5 provided with an image receptor 11, e.g. a cassette holder, against which the breast is compressed by means of a compression element 6, for example a compression paddle. The compression element 6 is mounted on the C-arm to move relative thereto in substantially radial directions (arrow B) and the C-arm is adapted to move essentially in the traveling direction of the compression element 6 transversely to the turning axle 2 (traveling direction of C-arm is indicated by arrow A). The unit is further provided with control elements 20, 21 for controlling the motorized linear action of the C-arm and the compression element to occur concurrently. In concurrent action or movement, the traveling speeds are substantially equal to one another regardless of a compression resistance encountered by the compression element. Such a compression resistance resulting from compression of the breast decelerates the compression element traveling speed and simultaneously the C-arm traveling speed, said traveling speeds remaining equal to each other. The unit driving means preferably comprise a foot pedal 7, shown in FIG. 7 and provided with an individual pedal element 8 and 9 for each movement as well as means 10 for operating each pedal element concurrently, if necessary. The means 10 comprises for example a pedal mounted upon the pedals 8 and 9, the use of such pedal resulting in concurrent operation of both pedals 8, 9. As an alternative, the driving means may consist of sound-activated control elements.

Figure 2:
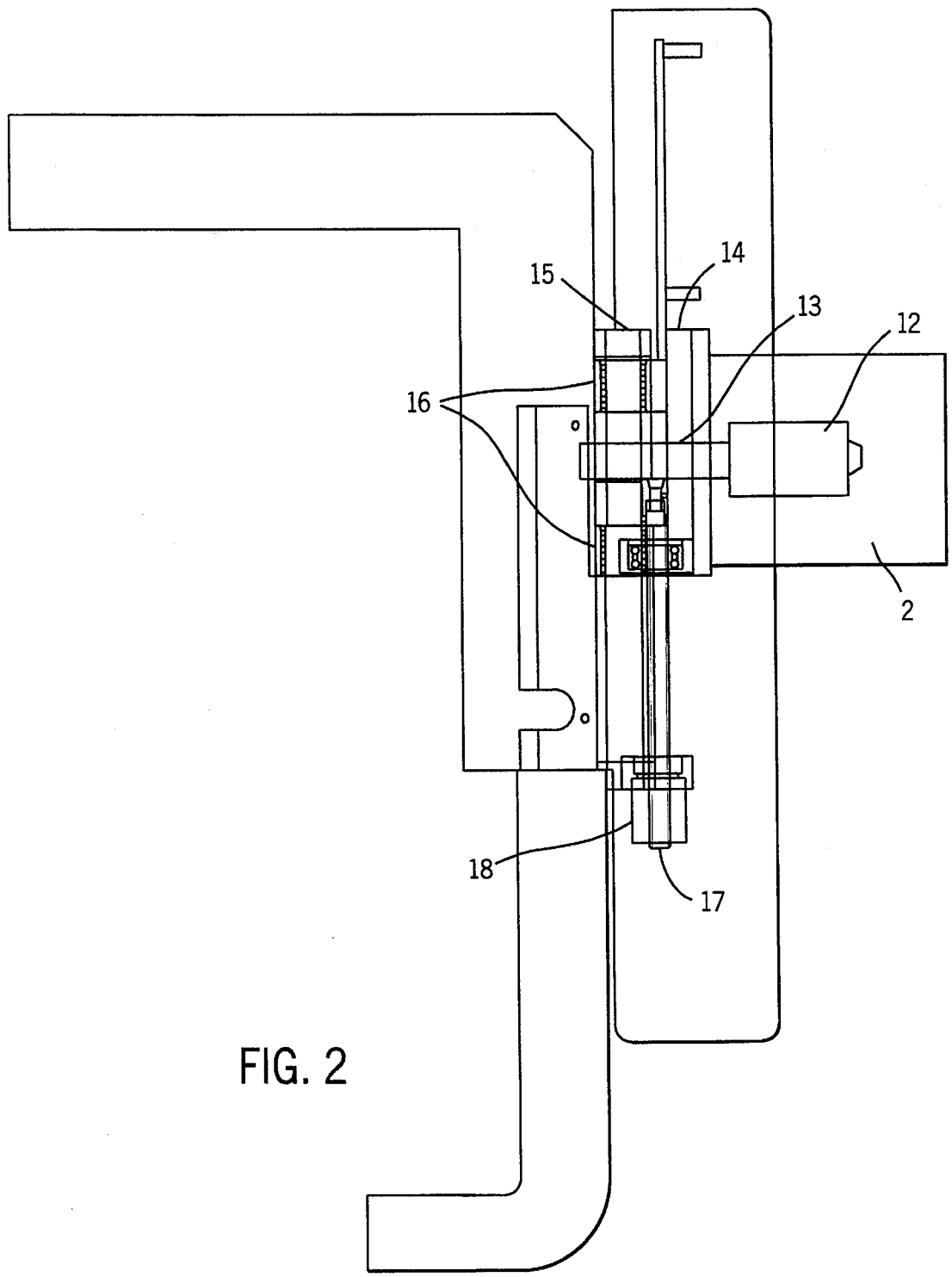
FIGS. 2 and 3 show one detail in a unit of the invention in a side view and in a front view, respectively.
Figure 3:
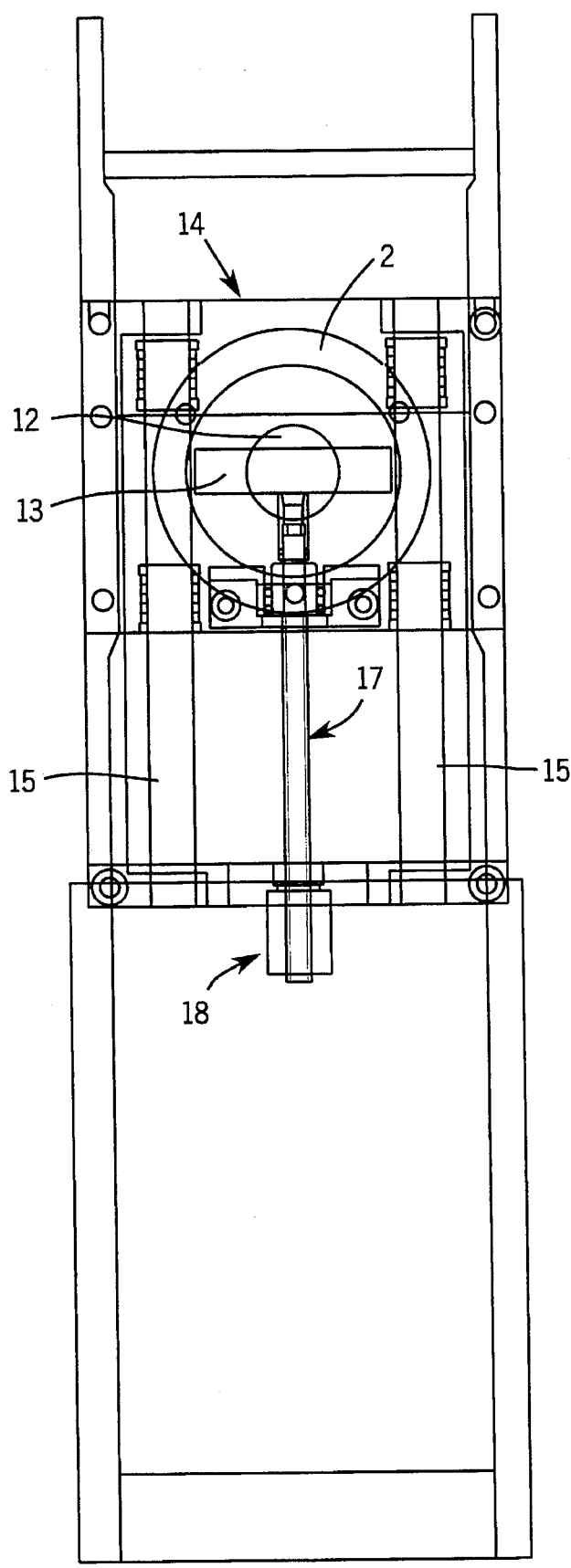

FIGS. 2 and 3 illustrate in more detail elements for implementing linear movement of the C-arm relative to the turning axle 2. These elements comprise a motor 12, which is included in the tube 2 and which, e.g. by means of a worm gear 13, drives a flat-thread screw 17 journalled to a flange 14 included in the tube. Turning of the flat-thread screw 17 translates into movement of the C-arm through the intermediary of a flat-thread nut 18 by means of guides 15. The guides 15 are in contact with the C-arm and extend through ball sockets 16 which are in contact with the flange 14.

According to FIG. 4, the control means for controlling linear motorized movement of the C-arm and compression movement of the compression element to occur concurrently in view of compressing the breast between the compression element and the image receptor comprise an element 20, for example a tachometer, which measures the linear movement speed of the compression element and which measures the rotating speed of a drive shaft (not shown) for control guides 22 intended for the compression element 6 and which delivers a reference signal to an electronic control unit 21 which, in turn, issues a control command to a monitor 12 for driving the flat-thread screw 17, such that the C-arm will have a linear speed which is substantially equal but reversed to the speed of the linear movement of the compression element 6. Instead of a tachometer it is conceivable to employ various mechanical, magnetic, electronic or like traveling-speed measuring means, known as such to a skilled person.

Figure 5:
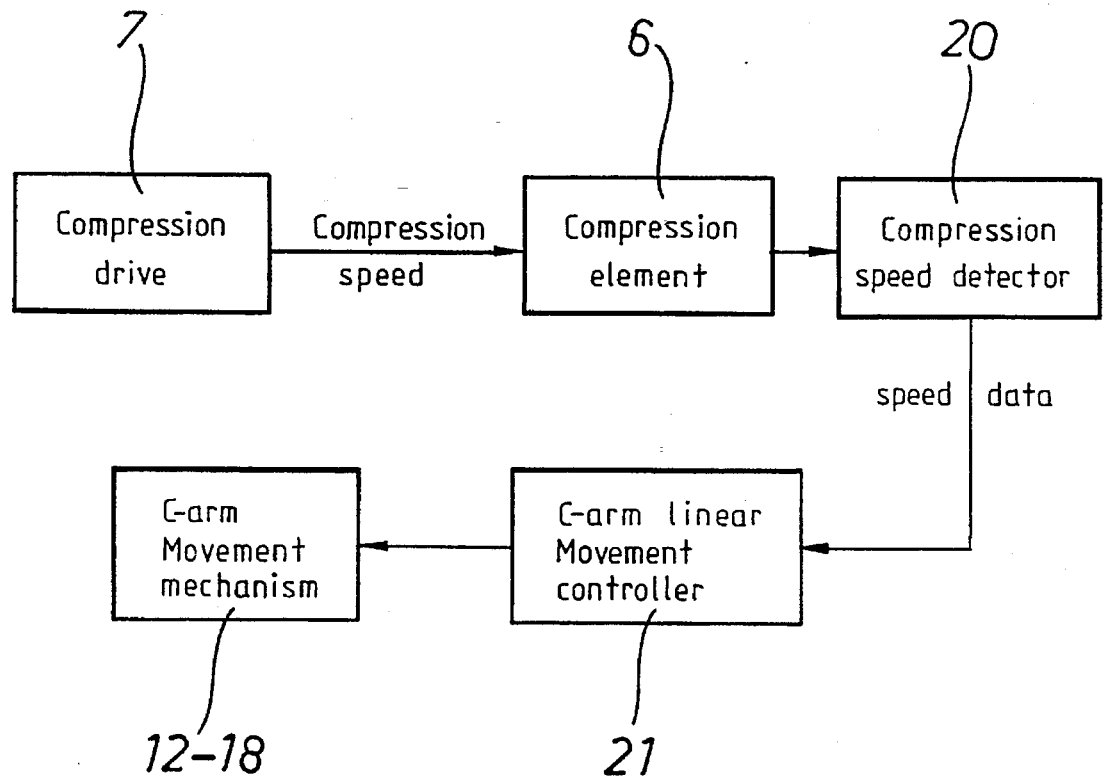
FIG. 5 is a schematic view of a control system for the unit.

FIG. 5 illustrates schematically an arrangement for controlling the linear-movement speed of the C-arm in response to the linear-movement speed of the compression element. As shown in the figure, the compression element driving means 7 provide a command for moving the compression element 6 relative to the C-arm, the speed detector 20 measuring the real traveling speed of the compression element 6 and delivers speed data to the C-arm linear movement control unit 27, which in turn provides a control command for the C-arm movement mechanism 12–18 for adjusting the C-arm linear movement speed to be substantially equal to the measured speed of the compression element. With this arrangement, it is possible to take into account the deceleration of the compression element traveling speed caused by the compression resistance, such that the compression element and the C-arm will have traveling speeds which remain substantially equal to each other throughout the process.

We claim:

1. A mammography unit, comprising a C-arm which is mounted on a turning axle (2) adapted to be vertically (arrow C) movable on an upright column (1) and which is pivotable about the turning axle (2) (arrow D), one leg (3) of said C-arm being provided with an X-ray tube (4) and the opposite leg (5) with an image receptor, and said unit further comprising a compression element (6) for compressing the breast to be imaged against the image receptor, said C-arm being further adapted to move linearly (arrow A) in substantially radial directions in the direction transverse to the turning axle (2), in which unit the compression element (6) is mounted on the C-arm and travels essentially linearly relative to the C-arm lengthwise of the C-arm and simultaneously with the C-arm radially relative to the turning axle, said unit comprising elements for controlling the linear motorized movement of the C-arm (arrow A) and the relative compressive movement of the compression element (6) (arrow B) to occur simultaneously at a substantially equal but oppositely directed speed for compressing the breast between the compression element and the image receptor.

2. A unit as set forth in claim 1, wherein a tachometer is used for measuring the compression element traveling speed and for delivering a reference signal to a control unit which adjusts the C-arm linear speed accordingly.

3. A unit as set forth in claim 1, wherein the unit driving means comprise a foot pedal.

4. A unit as set forth in claim 1, wherein the unit driving means comprise sound-activated control elements.

5. A unit as set forth in claim 2, wherein the unit driving means comprise a foot pedal.

6. A unit as set forth in claim 2, wherein the unit driving means comprise sound-activated control elements.

\* \* \* \* \*